(12) United States Patent
Shaw et al.

(10) Patent No.: US 10,646,148 B2
(45) Date of Patent: May 12, 2020

(54) BODILY FLUID COLLECTION DEVICE WITH INTEGRAL TUBE SEAL

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 155 days.

(21) Appl. No.: 15/713,284

(22) Filed: Sep. 22, 2017

(65) Prior Publication Data

US 2019/0090798 A1    Mar. 28, 2019

(51) Int. Cl.
*A61B 5/15* (2006.01)
*A61M 5/158* (2006.01)
*A61B 5/153* (2006.01)

(52) U.S. Cl.
CPC ......... *A61B 5/15074* (2013.01); *A61B 5/153* (2013.01); *A61B 5/15003* (2013.01); *A61B 5/150389* (2013.01); *A61B 5/150503* (2013.01); *A61B 5/150656* (2013.01); *A61B 5/150732* (2013.01); *A61M 5/158* (2013.01); *A61M 2005/1583* (2013.01); *A61M 2005/1585* (2013.01); *A61M 2005/1586* (2013.01); *A61M 2005/1587* (2013.01)

(58) Field of Classification Search
CPC combination set(s) only.
See application file for complete search history.

(56) References Cited

U.S. PATENT DOCUMENTS

| | | | |
|---|---|---|---|
| 6,063,040 A | 5/2000 | Owen et al. | |
| 7,288,078 B2 | 10/2007 | Fitzgerald | |
| 8,469,927 B2 | 6/2013 | Shaw et al. | |
| 9,381,309 B2 | 7/2016 | Shaw et al. | |
| 2009/0306601 A1* | 12/2009 | Shaw | A61M 5/158 604/177 |
| 2014/0171876 A1* | 6/2014 | Shaw | A61M 5/3221 604/198 |
| 2016/0310677 A1 | 10/2016 | Shaw et al. | |

* cited by examiner

*Primary Examiner* — Bhisma Mehta
*Assistant Examiner* — Hamza A Darb
(74) *Attorney, Agent, or Firm* — Ross Barnes LLP; Monty L. Ross

(57) ABSTRACT

A medical device useful for collecting samples of a bodily fluid, typically a vascular fluid such as blood. The subject device can also be used for infusing liquids into a patient. The fluid flow path desirably includes a forwardly projecting, rearwardly biased needle, a needle holder and a length of plastic tubing, the forwardly extending end of which is configured to function as a fluid seal to reduce the likelihood of fluid leakage during or after use. Following use, the needle is retractable from the patient by sliding a needle retraction cavity transversely into longitudinal alignment with the needle, thereby disrupting the fluid flow path and propelling the needle rearwardly so that it no longer projects from the device.

10 Claims, 7 Drawing Sheets

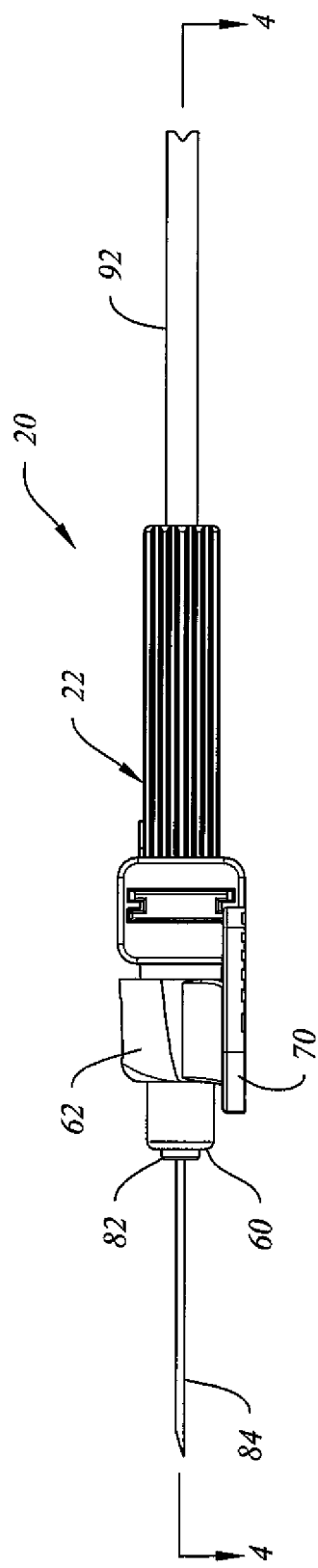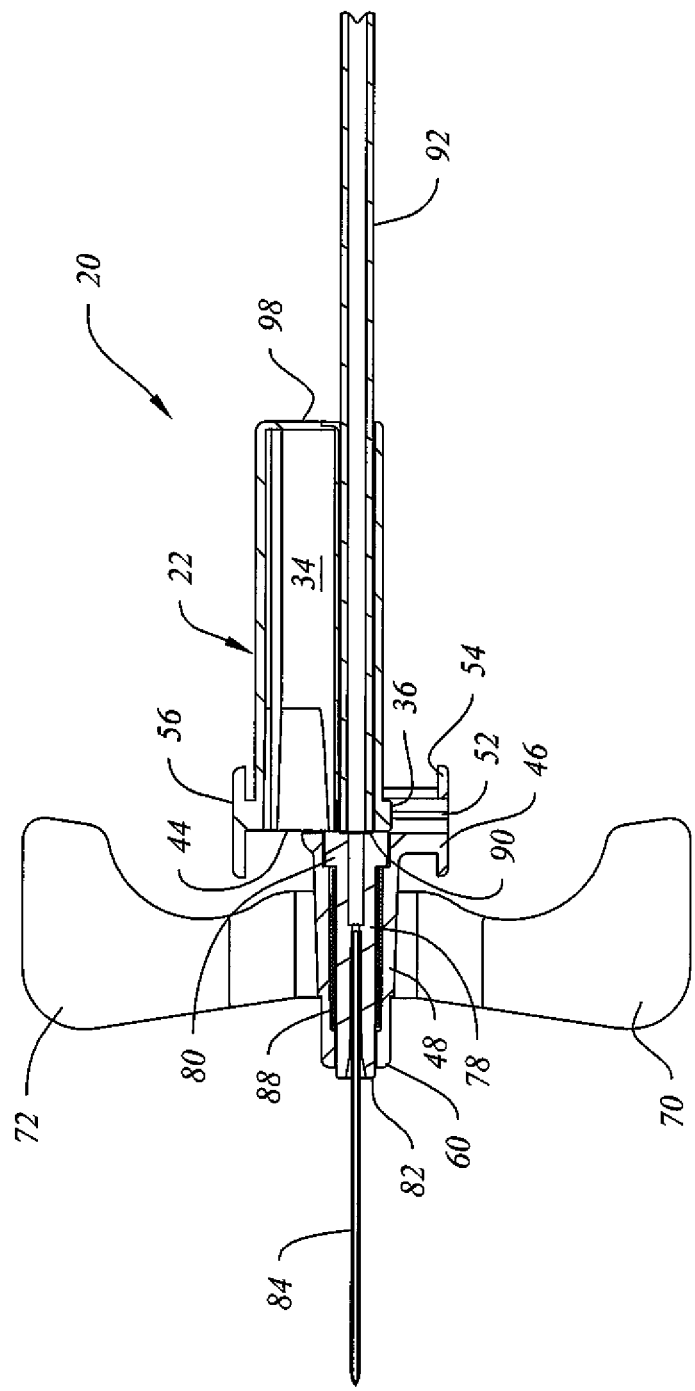

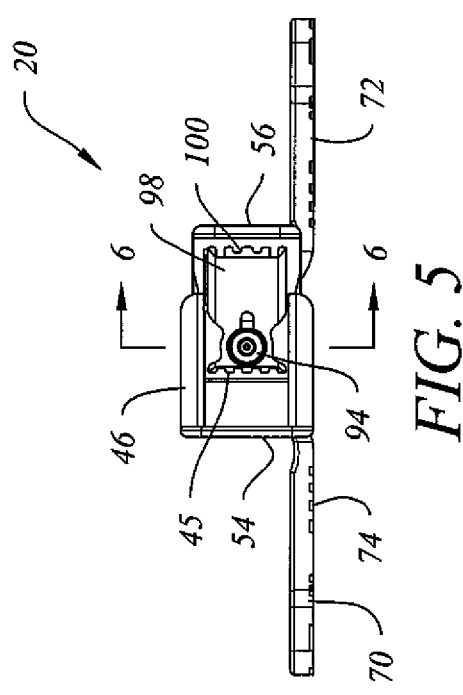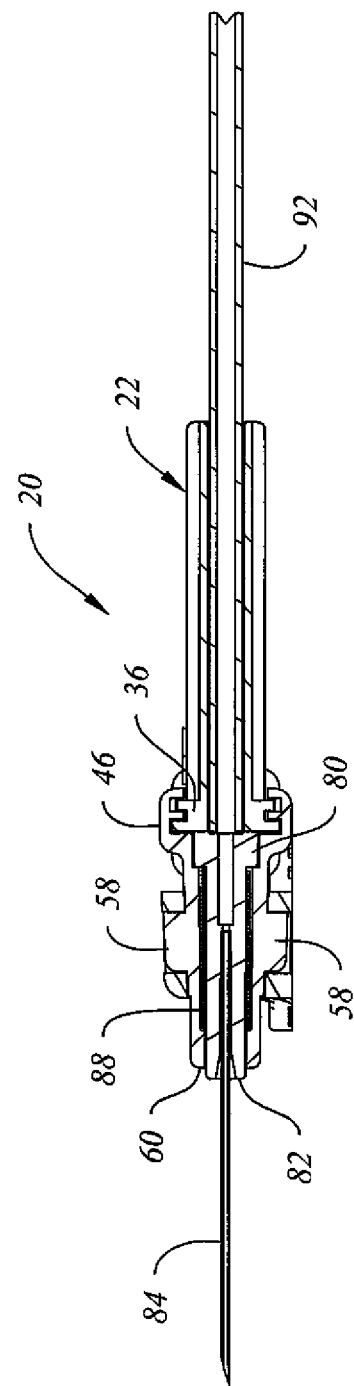

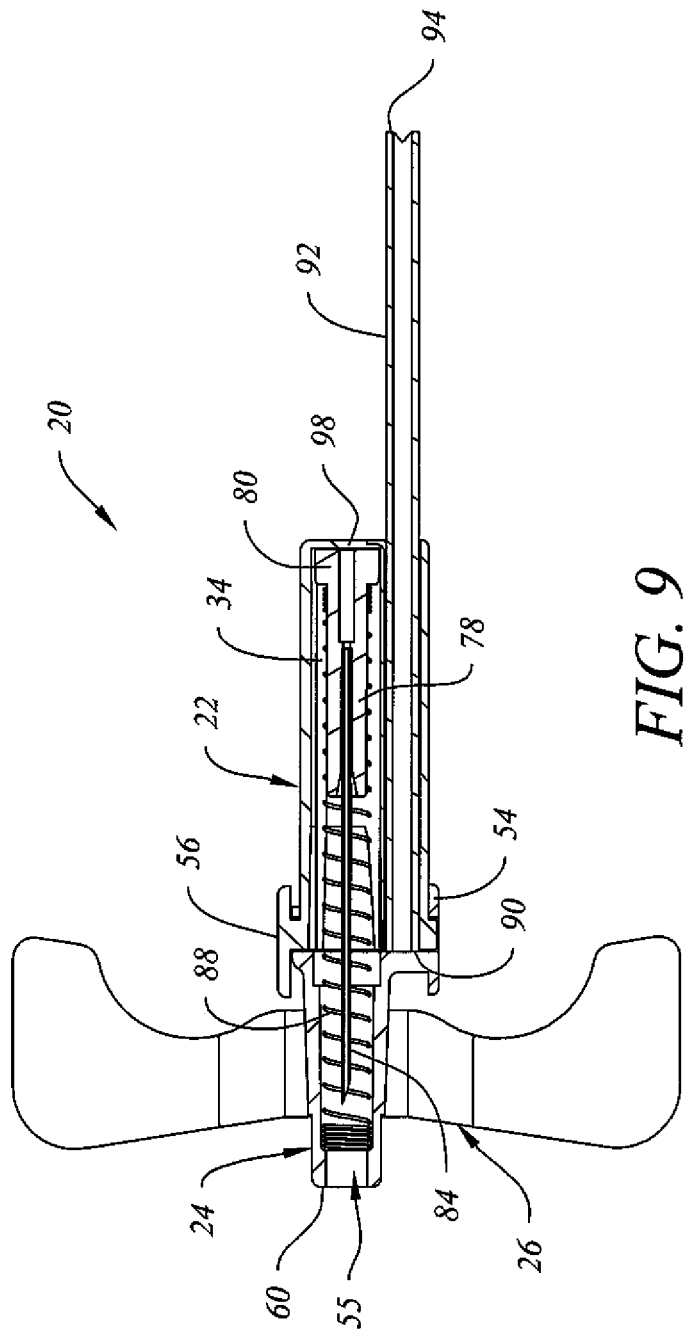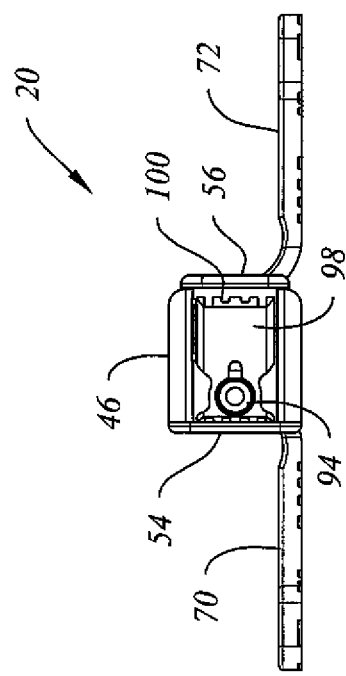

BODILY FLUID COLLECTION DEVICE WITH INTEGRAL TUBE SEAL

1. FIELD OF THE INVENTION

This invention relates to medical device useful for collecting samples of a bodily fluid, typically a vascular fluid such as blood, from a medical patient. Alternatively, the subject device can be used for infusing a liquid into the vascular system of a patient. This invention also relates to a fluid collection or infusion device that can be easily connected to a fluid receptacle or a fluid source by a flexible plastic tube and that is intended to be disposable following a single use. This invention also relates to a fluid collection or infusion device configured so that the forwardly extending end of the plastic tube functions as a fluid-tight seal in the fluid flow path and, following needle retraction, between two slidably engaged structural elements of the device. This invention also relates to a bodily fluid collection device or infusion device having a forwardly projecting, rearwardly biased needle that is retractable directly out of the patient and into the device following use by slidably repositioning a needle retraction cavity transversely into longitudinal alignment with the needle, thereby reducing the likelihood of accidental needle sticks and any resultant contamination of another with fluid-borne pathogens.

2. DESCRIPTION OF RELATED ART

A disposable bodily fluid collection or infusion device with a retractable needle are disclosed, for example, in U.S. Pat. No. 8,469,927. A frontal attachment device for a syringe with pinch-activated needle retraction is disclosed, for example, in U.S. Pat. No. 9,381,309.

SUMMARY OF THE INVENTION

A medical device is disclosed that is useful for collecting samples of a bodily fluid, typically a vascular fluid such as blood. The subject device can also be used for infusing liquids into a patient. The fluid flow path desirably includes a forwardly projecting, rearwardly biased needle, a needle holder and a length of plastic tubing, the forwardly extending end of which is configured to function as a fluid seal to reduce the likelihood of fluid leakage during or after use. Following use, the needle is retractable from the patient by sliding a needle retraction cavity transversely into longitudinal alignment with the needle, thereby disrupting the fluid flow path and propelling the needle rearwardly so that it no longer projects from the device.

According to one embodiment, the subject medical device comprises a body, a frontal attachment, a length of flexible plastic tubing, and a needle retraction assembly seated inside the frontal attachment, the needle retraction assembly further comprising a rearwardly biased needle holder and a needle that projects forwardly from the frontal attachment prior to and during use of the subject medical device. The body and frontal attachment are desirably cooperatively configured to be connected together in sliding relationship to each other in such manner that transverse slidable movement of the body toward the frontal attachment and the longitudinal axis through the needle during use of the subject medical device disrupts the fluid flow path through the device and allows the needle holder and needle to be forced rearwardly to a position in which the needle tip is protected inside the device. A wing member having opposed, laterally extending wings and a hub attachable to the needle support tube of the frontal attachment is also desirably provided to improve the stability of the device relative to a patient during use of the device.

According to another embodiment, the proximal end of the plastic tubing cooperates with the rearwardly extending end of the needle holder to establish a fluid seal around the fluid flow path through the needle holder and plastic tubing and reduce the likelihood of fluid leakage out of the fluid flow path between the body and the frontal attachment during use of the device. The plastic tubing is desirably attached, such as by gluing or another similarly effective means, to the fluid flow channel inside the body to prevent axial movement of the proximal end of the compressible plastic tubing relative to the front opening of the fluid flow channel. When, during assembly of the device, the slide block of the frontal attachment is attached to the slide mount of the body in a position where the rearwardly biased head of the needle holder is aligned with and abutting the forwardly facing surface of the proximal end of the plastic tubing, the plastic tubing compresses slightly to create a fluid seal. Later, following use of the device, when the body is moved transversely relative to the longitudinal axis of the needle and the needle support tube of the frontal attachment to initiate needle retraction, the proximal end of the plastic tubing slides off the head of the needle holder and expands against the rearwardly facing surface of the slide block of the frontal attachment, thereby again maintaining a fluid seal as to liquid remaining inside the fluid flow channel of the body following disruption of the fluid flow path during needle retraction.

BRIEF DESCRIPTION OF THE DRAWINGS

The apparatus of the invention is further described and explained in relation to the following drawings wherein:

FIG. 3 is a right side elevation view of the device of FIG. 1;

FIG. 4 is a cross-sectional plan view taken along line 4-4 of FIG. 3;

FIG. 5 is a rear elevation view of the device of FIG. 1;

FIG. 6 is a cross-sectional view taken along line 6-6 of FIG. 5;

FIG. 9 is a cross-sectional plan view taken along line 9-9 of FIG. 8; and

FIG. 10 is a rear elevation view of the device of FIG. 7.

DESCRIPTION OF THE PREFERRED EMBODIMENTS

Figure 1:
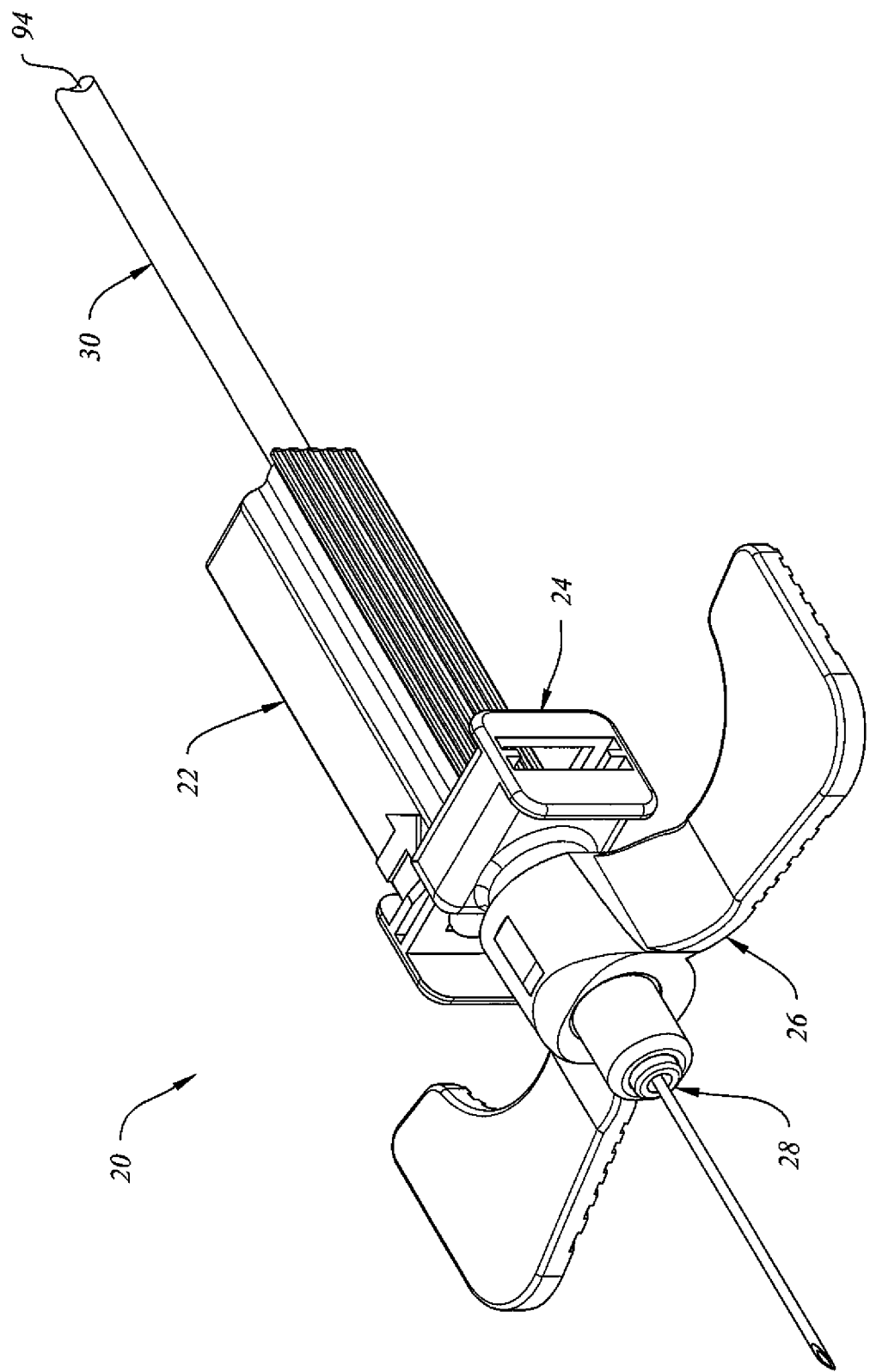
FIG. 1 is a front perspective view of one embodiment of a bodily fluid collection and infusion device of the invention with the needle uncapped and projecting forwardly in its unretracted position.

Referring to FIG. 1, medical device 20 comprises body 22, frontal attachment 24, wing member 26, needle retraction assembly 28 and flexible plastic tubing 30. Distal end 94 of flexible plastic tubing 30 is depicted in the drawings as being of indeterminate length and without a connector or fitting, as it will be apparent to those of ordinary skill in the art upon reading this disclosure in relation to the accompanying drawings that several different types of convention, commercially available connectors, clamps and end fittings can be provided and used with the subject device depending upon the configuration of the fluid receptacle or fluid source with which medical device 20 is used.

Figure 2:
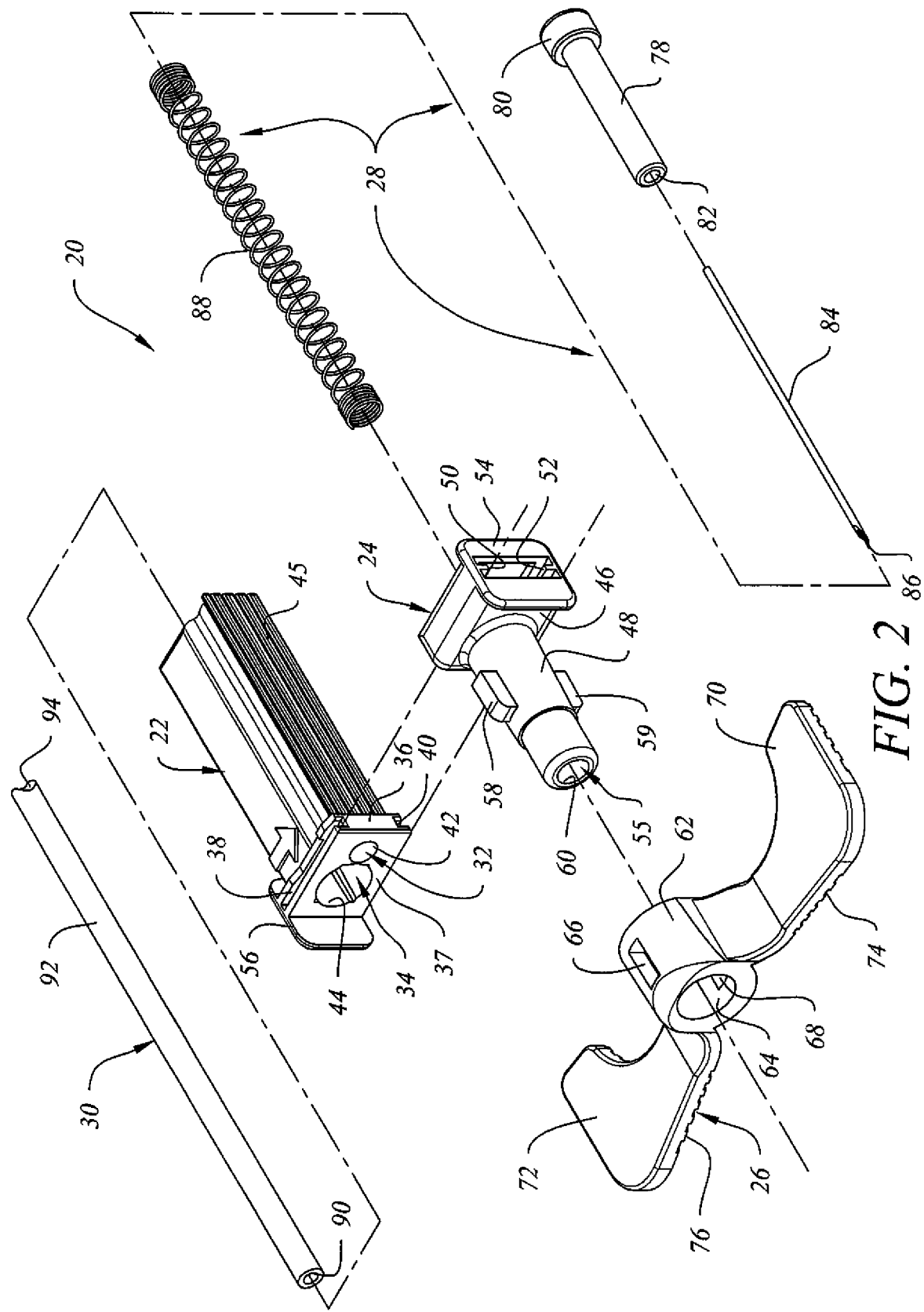
FIG. 2 is an exploded front perspective view of the device of FIG. 1.

Referring to FIG. 2, body 22 further comprises a longitudinally extending fluid flow channel 32 having an open front end 42 and a corresponding open back end (not visible in FIG. 2), and another longitudinally extending, laterally spaced-apart needle retraction cavity 34 having an open front end 44 and a closed back end. Body 22 further comprises slide mount 36 comprising upper and lower laterally extending recesses 38, 40, a forwardly facing surface 37 and a touch surface 56 facing laterally outward from needle retraction cavity 34. Textured outer surface 45 is also provided for the benefit of a medical practitioner handling the device.

Medical device 22 further comprises a flexible plastic tubing 30 having a tubular outer wall 92 of indeterminate length as signified by truncated distal end 94, and a forwardly facing proximal end 90. Flexible plastic tubing 30 is desirably sized to be inserted inside fluid flow channel 32 of body 22 during assembly or prior to use, and desirably has an outside diameter slightly less than the inside diameter of fluid flow channel 32 to permit such insertion. According to various embodiments of the invention, proximal end 90 of flexible plastic tubing 30 can be held in substantially fixed axial relation to the inside wall of fluid flow channel 32 by friction or by using a suitable glue or adhesive, or by laser welding or by a clamping device so that proximal end 90 of flexible tubing 30 does not slide axially inside fluid flow channel 32 during use of medical device 20. According to one embodiment of the invention, proximal end 90 extends slightly forward of open front end 42 and forwardly facing surface 37 of slide mount 36 so that it can cooperate with the rearwardly facing end 80 of the needle holder to create a fluid seal around the fluid flow path between body 22 and frontal attachment 24 during assembly and use. The rearwardly facing annular surface of rearwardly biased needle holder, discussed in greater detail below, can desirably slightly compress proximal end 90 of flexible plastic tubing 30 during assembly to help effectuate the fluid seal.

Frontal attachment 24 of medical device 20 preferably further comprises slide block 46 having transverse, laterally extending upper and lower rails 50, 52 slidably engageable with laterally extending upper and lower recesses 38, 40 of body 22 to provide transverse sliding engagement between body 22 and frontal attachment 24. Needle support tube 48 desirably projects forwardly from slide block 46. Touch pad 54 desirably faces laterally outward to provide a surface for the application of digital pressure to resist intradermal movement of needle 84 if digital pressure is applied to touch pad 56 of slide mount 36 during use of the device or during needle retraction following use. Needle support tube 48 further comprises stepped internal bore 55 comprising annular internal seating surfaces for the needle retraction mechanism as discussed in greater detail below. Front opening 60 of needle support tube 48 is desirably sized and configured to allow the forwardly extending end 82 of the needle holder and the front portion of needle 84 and needle tip 86 to project forwardly from needle support tube 48.

One embodiment of needle retraction mechanism 28 desirably further comprises a needle holder 78 with a front end 82, a larger-diameter head 80 and an elongate shaft section 78 that supports spring 88 while in compression during use and prior to needle retraction. Both head 80 and the forwardly extending end of compression spring 88 are desirably seated on rearwardly facing annular surfaces inside stepped inside bore 55 of frontal attachment 24, and needle 84 is desirably glued inside the longitudinal bore through the needle holder. During assembly, the needle holder is inserted into the coils of spring 88, which are compressed as they are inserted into the rear of stepped inside bore 55 of needle support tube 48. While spring 88 is compressed, slide block 46 of frontal attachment 24 is slidably engaged with slide mount 36 of body 22.

Wing member 26 desirably further comprises opposed, laterally extending wings 70, 72 having texture undersides 74, 76, respectively, to reduce the likelihood of slippage between the undersides and the skin of a patient with which they are in contact during use of device 20. Hub 62 comprises bore 64 and opposed slots 66, 68 that are engageable with needle support tube 48 and its outwardly projecting lugs 58, 59 during assembly of medical device 20.

FIGS. 3-6 depict various previously identified views of the assembled elements as discussed above. It will be apparent to those of skill in the art upon reading this disclosure that a needle cap is not depicted in the drawings but would be provided to protect the forwardly projecting needle tip 86 (FIG. 2) prior, to use. Such a needle cap will frictionally engage the outside wall of the needle support tube 48 forwardly of wing member 26 and is easily removable and disposed of just prior to inserting needle 84 into a patient.

Figure 7:
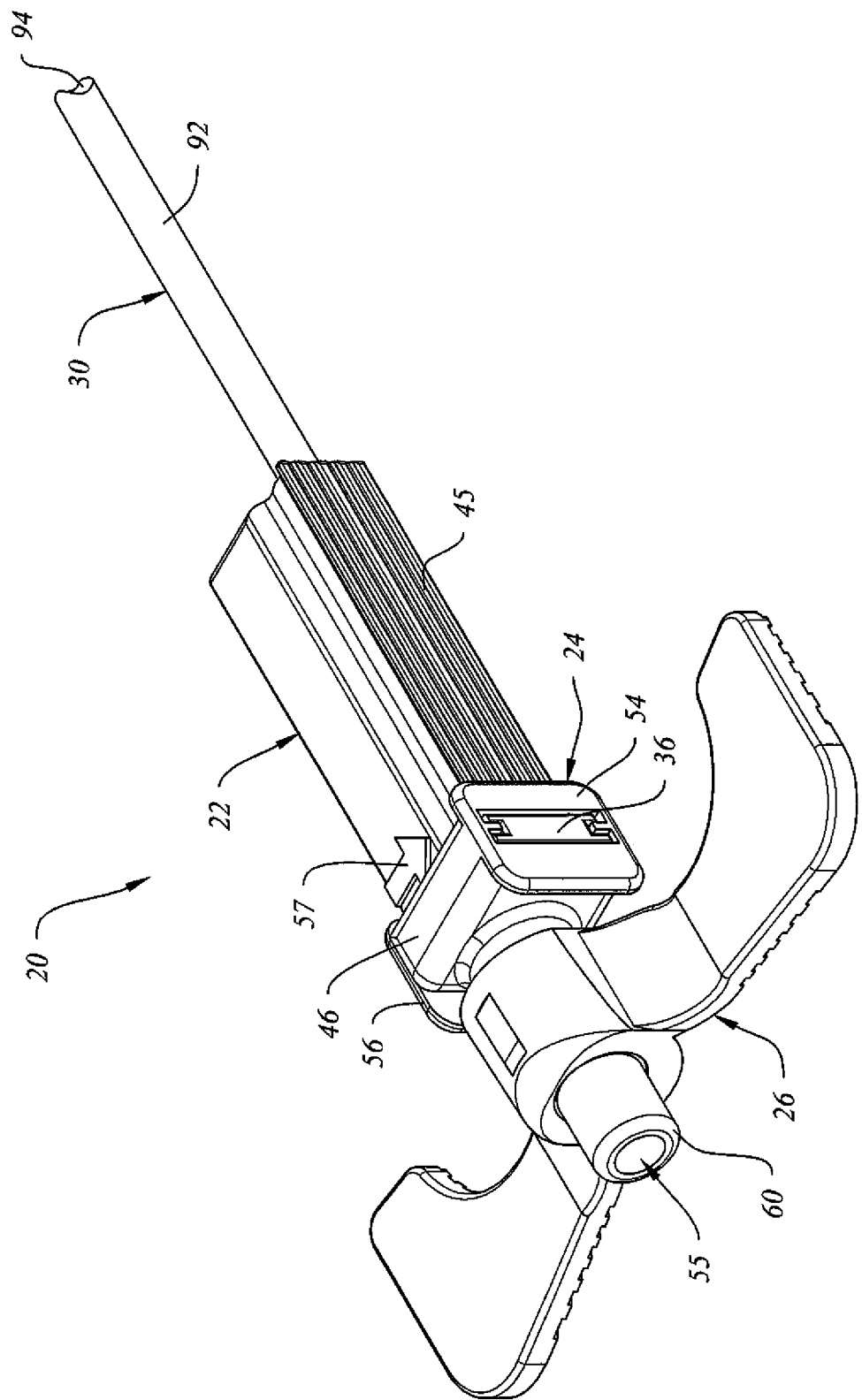
FIG. 7 is a front perspective view of one embodiment of the device of FIG. 1 with the needle retracted following use.
Figure 8:
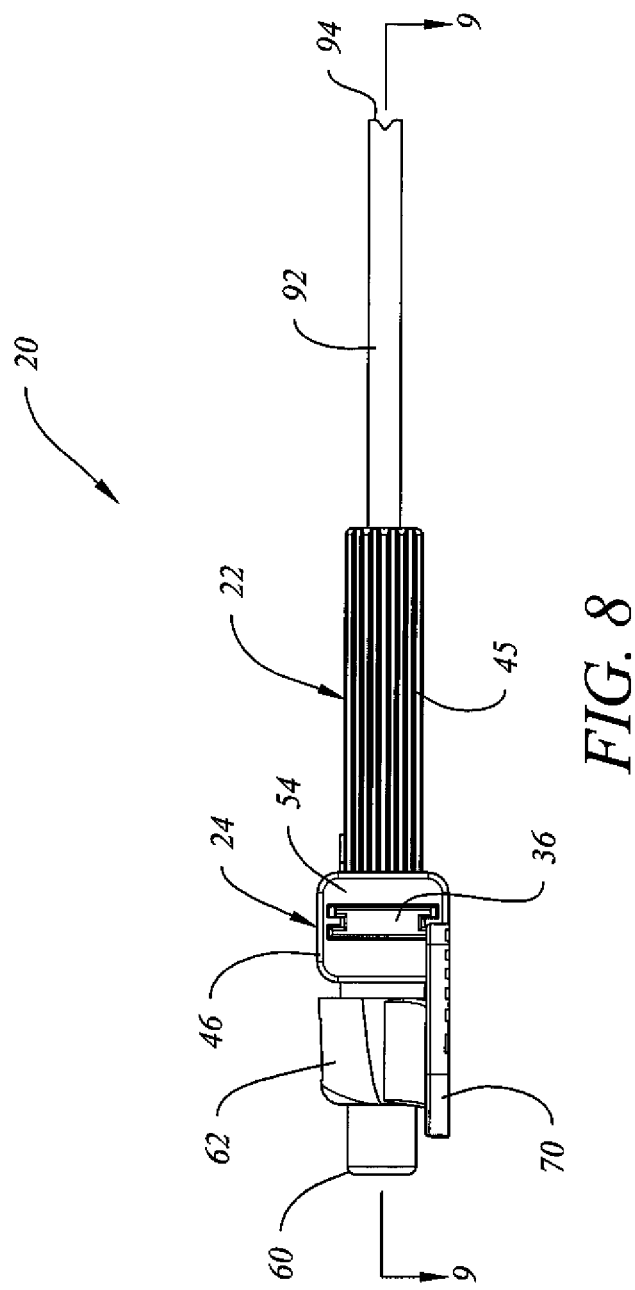
FIG. 8 is a right side elevation view of the device of FIG. 1 with the needle retracted following use.

FIGS. 7-10 similarly depict the position of elements previously discussed following needle retraction following use of medical device 20. Referring to FIG. 7, arrow 57 indicates the direction that body 22 is moved relative to slide block 46 of frontal attachment 24 to initiate needle retraction, preferably while the needle is still inserted into the skin of the patient with which medical device 20 is being used. Referring specifically to FIG. 9, the fluid flow path through plastic tubing segment 92 is disrupted and proximal end 90 is abutting the rearwardly facing surface of frontal attachment 24 to prevent fluid leakage back out the front of medical device 20 following needle retraction. Needle 88 is fully contained inside medical device 20 to protect the user, patient and bystanders or subsequent handlers of medical device 20 from accidental needle sticks and possible contamination by fluid-borne pathogens during fluid collection procedures.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventor(s) and/or Applicant are legally entitled.

What is claimed is:

1. A medical device useful for collecting a bodily fluid from the medical patient or for infusing a liquid into a vascular system of the medical patient, the device comprising:
   a body further comprising a cylindrical fluid flow channel extending longitudinally through the body and having an open front end and an open back end, and a substantially cylindrical needle retraction cavity disposed in parallel and laterally spaced-apart relation to the fluid flow channel, the needle retraction cavity having an open front end and a closed back end, and a slide mount having recesses disposed transversely above and below the open front end of the fluid flow channel and the open front end of the needle retraction cavity;

a length of flexible, compressible plastic tubing disposed inside the fluid flow channel, the flexible, compressible plastic tubing having a proximal end extending forwardly of the open front end of the fluid flow channel, and a distal end disposed rearwardly of the body, the proximal end of the flexible, compressible plastic tubing being attached to the body and the distal end being releasably attachable to a fluid receptacle or a fluid source external to the device;

a frontal attachment further comprising a slide block having transverse, laterally extending upper and lower rails slidably engaging the recesses in the slide mount of the body, and a needle support tube having a stepped longitudinal bore; and a needle retraction assembly seated inside the frontal attachment, the needle retraction assembly comprising a rearwardly biased retractable needle projecting forwardly from the frontal attachment, a needle holder establishing fluid communication with the proximal end of the plastic flexible, compressible tubing, and a spring biasing the needle holder and the retractable needle rearwardly;

wherein the proximal end of the plastic flexible, compressible tubing is compressed by a rear end of the needle holder to create a fluid seal between the needle holder and the plastic flexible, compressible tubing during use of the medical device for collecting the bodily fluid from the medical patient or for infusing the liquid into the vascular system of the medical patient; and wherein an application of digital pressure against the body following use of the medical device causes the needle retraction cavity to slide transversely relative to the slide block and into alignment with the needle, thereby allowing the spring to propel the needle rearwardly into a shielded position inside the medical device.

2. The medical device of claim 1 further comprising a wing member having a hub and two oppositely disposed wings, extending laterally outward from the hub.

3. The medical device of claim 2 wherein the needle support tube of the frontal attachment comprises a pair of radially extending, oppositely disposed lugs, and wherein the hub comprises a pair of slots configured to receive and engage the pair of lugs.

4. The medical device of claim 1 wherein the body further comprises a first touch pad facing laterally outward from the needle retraction cavity.

5. The medical device of claim 1 wherein the frontal attachment further comprises a second touch pad facing laterally outward from the needle retraction assembly.

6. The medical device of claim 1 wherein the body and the frontal attachment are each made of a moldable polymeric material.

7. The medical device of claim 1 wherein the spring has sufficient force to withdraw the needle from the medical patient and also propel the needle holder into the needle retraction cavity such that the entire needle is contained inside the medical device after the needle retraction cavity is activated by the application of digital pressure to slide the needle retraction cavity transversely into alignment with the needle.

8. The medical device of claim 7 wherein the proximal end of the flexible, compressible plastic tubing provides another fluid seal between the body and a rearwardly facing surface of the frontal attachment after the needle retraction cavity is activated by the application of digital pressure to slide the needle retraction cavity transversely into alignment with the needle.

9. The medical device of claim 1 wherein the bodily fluid is a vascular fluid.

10. The medical device of claim 9 wherein the fluid is blood.

* * * * *